(12) United States Patent
Sanz et al.

(10) Patent No.: US 6,376,722 B1
(45) Date of Patent: *Apr. 23, 2002

(54) LUTEIN TO ZEAXANTHIN ISOMERIZATION PROCESS AND PRODUCT

(76) Inventors: Vicente Ernesto Ridaura Sanz, Cuauhtemoc No. 245, Tepepan Xochimilcon C.P. 16020; Oscar Rubén García Correa, Marqués de la Laguna No. 159, Col. Lomas del Marqués C.P. 76146 Querétaro, Qro.; Armando Prado Naranjo, Calle Sierra Oriental No. 109, Col. La Sierrita C.P. 76135, Querétaro, Qro., all of (MX)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/181,657

(22) Filed: Oct. 29, 1998

(30) Foreign Application Priority Data

Oct. 31, 1997 (MX) .............................................. 978439

(51) Int. Cl.$^7$ ................................................ C07C 35/21
(52) U.S. Cl. ................... 568/816; 568/823; 568/834; 568/832; 568/822
(58) Field of Search ................ 568/816, 823, 568/822, 832, 834

(56) References Cited

U.S. PATENT DOCUMENTS

| | | | | |
|---|---|---|---|---|
| 3,523,138 A | * | 8/1970 | Grant | 568/816 |
| 3,535,426 A | | 10/1970 | Hawks | |
| 3,539,686 A | | 11/1970 | Rosenberg | |
| 3,558,712 A | | 1/1971 | Surmatis et al. | |
| 3,783,099 A | | 1/1974 | Matoushek | |
| 3,839,489 A | * | 10/1974 | Mahan | 585/747 |
| 3,872,178 A | * | 3/1975 | Tabler | 585/378 |
| 3,989,757 A | | 11/1976 | Surmatis | |
| 5,382,714 A | * | 1/1995 | Khachik | 568/834 |
| 5,523,494 A | * | 6/1996 | Torres-Cardona | 568/834 |
| 5,780,693 A | * | 7/1998 | Bernhard | 568/816 |
| 5,876,782 A | * | 3/1999 | Sas | 424/635 |

FOREIGN PATENT DOCUMENTS

| | | |
|---|---|---|
| MX | 1697 | 10/1971 |
| MX | 6010 | 3/1979 |
| MX | 6320 | 3/1979 |

OTHER PUBLICATIONS

CA:89:42408 abs of JP53009706, Jan. 1978.*
CA:107:38912 abs of React Kinet Catal Lett by Capka 31 (1) pp. 41–46, 1986.*
Chemical Abstracts No. 108463z, vol. 73, 1970.
Chemical Abstracts No. 145473d, vol. 89, 1978.
Chemical Abstracts No. 16923v, vol. 79, 1973.
Andrews, A. G., "Isomerization of ε–Carotene to β–Carotene and of Lutein to Zeaxanthin", *Aeta Chem. Scand.*, B 28, No. 1 (1974).
Fletcher, D.L. et al., "The Effect of Saponification on the Broiler Coloring Capability of Marigold Extracts", *Poultry Science J.*, 65:1708–1714 (1986).
Janky, D.M. et al., "The Influence of Different Xanthophyll Containing Feedstuffs on Pigmentation of Broilers Reared in Open and Windowless Houses", *Poultry Science J.*, 64:925–931 (1985).
Karrer, P. et al., "Umvandlung von α–Carotin in β–Carotin und von Xanthophyll in Zeaxanthin", *Helv. Chim. Acta.*, 30:266–267 (1947).

* cited by examiner

*Primary Examiner*—Jean F. Vollano
(74) *Attorney, Agent, or Firm*—Rothwell, Figg, Ernst & Manbeck

(57) ABSTRACT

A lutein to zeaxanthin isomerization process which includes a saponification or alkali treatment of a plant extract containing lutein followed by a heating period under controlled conditions, is carried out in the presence of a surface active agent having an HLB of from 1 to 40 as a catalyst for the lutein to zeaxanthin isomerization reaction, at a temperature between 70 to 140° C., in order to obtain a reaction product with high zeaxanthin concentrations of up to 80% of the total carotenoids.

10 Claims, No Drawings

LUTEIN TO ZEAXANTHIN ISOMERIZATION PROCESS AND PRODUCT

FIELD OF THE INVENTION

The present invention is related to the obtainment of natural pigments from plant materials for use as food additives and, more particularly, it is related to a lutein to zeaxanthin isomerization process and to the product obtained with the same.

DESCRIPTION OF THE PRIOR ART

As consciousness towards the potential harm caused by some synthetic pigments previously used in foodstuffs for humans and animals is awakening throughout the world, the use of natural plant pigments has acquired more and more importance. It is because of this reason that extraction of colorants from natural sources such as flowers and fruits has been carried out for a long time all over the world.

In the Book "Colorantes Naturales de Mexico", published by Industrias Resistol S. A. in 1988, several extraction methods of "flower dyes" are described, which comprise steps such as milling or boiling flower petals, and further addition of substances such as 96° ethyl alcohol, alum and vinegar solutions. This book also describes a vast plurality of different applications of several colorants of natural origin.

Among such applications and particularly in the poultry industry, the yellow color of egg yolk and broiler skin is originated by the pigments contained in the feed these birds ingest. The importance of pigmentation is that a good pigmentation in the birds is associated with a good condition and high quality during the breeding of the broilers, which has become an essential factor for the chicken and egg commercialization.

The main compounds associated with skin pigmentation in broilers and egg yolk pigmentation in laying hens (as well as in other species like fishes and crustaceans) are the so-called carotenoids, which are related to carotene in its chemical structure. The main carotenoids associated with pigmentation in poultry industry are denominated, in general terms, as xanthophylls (from Greek roots: Xanthos=Yellow; and Phylos=friend, lover). Xanthophylls have the common characteristic of being water insoluble pigments that are slightly soluble in ethyl alcohol and ether.

These carotenoids are generally found in natural products such as alfalfa, corn gluten, marigold flower and chili, among others.

Traditional sources of xanthophylls involved in poultry pigmentation have been alfalfa and corn gluten, in which carotenoids are found in their free form.

Market demand has compelled aviculturists to intensify the pigmentation level in their products, thus compelling also the natural pigment industry to carry out research and development activities for finding alternative natural sources of carotenoids. Marigold flower (*Tagetes erecta*) has become a viable alternative for these purposes due to its high xanthophyll content, although these compounds are found in its esterified form therein.

Nowadays, marigold flower yellow pigments and pigments from other plant sources are commercialized in its saponified form and formulated in different solid or liquid vehicles. Such pigments have been used for more than four decades as food additives, mainly as colorants for skin pigmentation in broilers and egg yolk pigmentation in laying hens. Saponification of said yellow pigments is necessary to facilitate their absorption and assimilation by the birds, inasmuch as these pigments, which are in their esterified form, are hydrolyzed or converted into their free form after saponification, thus being absorbed by the birds more rapidly and efficiently.

In the Poultry Science journal, pages 1708 to 1714, volume 65 of 1986, an article by D. L. Fletcher et al was published, in which the effect of saponification of marigold flower extracts and their pigmenting capacity in egg yolk and broiler skin is analyzed.

In industry, pigment extraction from marigold flower, as well as from other plant varieties, is traditionally carried out by means of different kinds of solvents to form concentrated extracts containing carotenoids in the esterified form, usually called oleoresins, oily extracts or crude extracts. In order to achieve a higher pigmenting capacity, the xanthophyll containing extracts are further treated to hydrolyze the esterified xanthophylls, generally by means of saponification processes.

In order to obtain the free form of such pigments, there is a variety of processes to hydrolyze xanthophylls, such as the process described in U.S. Pat. No. 3,783,099, granted on Jan. 1, 1974, in which the plant material containing xanthophylls is mixed with an enzyme such as cellulase, protease, etc. and a chelating agent such as ethylenediamine tetraacetic acid (EDTA), which achieves the hydrolysis of the esters at constant pH conditions and carries away the xanthophylls in their free form, thus avoiding a further saponification step.

At industrial scale, the most common hydrolysis process used, as mentioned above, is the saponification or alkali treatment of plant extracts. The state of the art acknowledges a variety of saponification processes of esterified xanthophylls from plant extracts.

U.S. Pat. No. 3,523,138, granted on Aug. 4, 1970, describes several processes for treating marigold flower extracts by means of aqueous solutions of alkali metal hydroxides in the presence of low molecular weight alkyl alcohols, in which temperatures ranging from 0 to 150° C. can be used with reaction times of between 1 minute and 8 hours, depending on the temperature employed, since the reaction time is reduced when the temperature is increased. This patent states that, in order to obtain an optimum result at 90° C., the process should take 3 hours.

Mexican Certificate of Invention No. 1697, granted on May 4, 1978, describes a process for obtaining a powdered pigmenting concentrate with enhanced activity, starting from oleoresins containing xanthophylls, in which the xanthophylls contained in marigold flowers are extracted using solvents such as chloroform, hexane or acetone, that are removed in a later stage, thus obtaining a pasty mass containing xanthophylls, fats, resins and waxes, which were carried away by the solvent. Once xanthophylls are extracted, an emulsion is formed by means of a surfactant, for instance a detergent, in order to assist in the incorporation of the pasty mass in aqueous alkali solutions, such as ammonium hydroxide, potassium hydroxide or sodium hydroxide, in order to carry out saponification at a temperature of from 50 to 90° C. during a period of time of from 15 to 60 minutes, after which an antioxidant and a xanthophyll fixer such as lecithin, as well as a substance that adheres to xanthophylls such as carboxymethyl cellulose, gelatin or palmitates are added. The solution obtained is then neutralized using a precipitating agent such as phosphoric acid, silicic acid or magnesium chloride, in order to neutralize and carry away the xanthophylls. Finally, the precipitate formed is filtered, washed, dried and ground in order to obtain the final powdered pigment.

In the prior art discussed in the above referred to Certificate of Invention, it is established that until that moment, no process for the obtention of powdered pigmenting concentrates starting from xanthophyll oleoresins in order to enhance their activity, had ever been conceived.

Mexican Certificate of Invention No. 6010, granted on Sep. 24, 1984, describes a process for obtaining a stable xanthophyll pigmenting concentrate from marigold flower, comprising the steps of extracting oil from marigold flowers using a solvent; saponifying the oily extract-solvent mixture with an alkali at a temperature of from 55 to 65° C. at atmospheric pressure; removing the solvent for obtaining a xanthophyll-rich concentrate, and stabilizing the concentrate by means of the addition of an antioxidant selected from ethoxyquin and ascorbic acid.

In the prior art discussed in Certificate of Invention No. 6010, several documents are cited, including the Mexican Certificate of Invention No. 1697. In these documents, it is possible to ascertain the research and development carried out from the year 1915 in the field of xanthophylls, as well as in their pigmenting effects and the different ways to achieve the xanthophylls saponification. It is important to mention that the novelty of the process claimed in Mexican Certificate of Invention No. 6010 was the fact that the saponification process was carried out in dry conditions and no further neutralization step was required.

Mexican Certificate of Invention No. 6320, granted on Apr. 1, 1985, describes an improved process for obtaining stabilized liposoluble extracts starting from vegetable raw materials (such as marigold flower), in which the base plant extract is saponified with a concentrated sodium and/or potassium hydroxide solution at a temperature within the range of from 60 to 90° C. in the presence of an emulsifier-thickener, such as carboxymethyl cellulose, gelatin or soluble starch. During the process for obtaining the extract, the humidity is controlled and the saponification reaction is carried out under vacuum or reduced pressure conditions within 0.1 and 0.05 atm, considering an average reaction time of 3 hours for obtaining a yield of from 95 to 100% saponification.

The discussion of the prior art cited in Mexican Certificate of Invention No. 6320, states that the main drawback of xanthophyll powdered extracts is their instability due to the powder surface contact with the oxygen of the atmosphere, including the containers where they are contained. This document claims as a novelty a process in which metallic precipitating agents and stabilizers are used to improve the properties of the powdered pigments, as well as the saponification reaction carried out under vacuum conditions.

An additional aspect related to the final shade of egg yolk or broiler skin is the fact that such tonality is important according to the requirements of the different markets where this kind of pigments are used as food additives. In some markets, such as the oriental market, orange to red shades are clearly preferred, and this is why the producers of this kind of additives have taken care of developing processes and products tending to satisfy these requirements.

Among the xanthophylls usually extracted from marigold flower in esterified form, lutein and zeaxanthin may be found, with lutein being found in a higher ratio (80%). For this reason, lutein is also known as xanthophyll since it exists in largest quantities in nature.

U.S. Pat. No. 3,569,386, granted on Nov. 10, 1970, describes several compositions containing carotenoids which, when added as food additives for laying hens, give several tonalities in the resulting egg yolks. Similarly, in the Poultry Science journal, page 925, volume 64 of 1985, a study was published which refers to the influence of the type of xanthophylls coming from different sources, which are used as food additives.

In order to get the orange-red tonalities, traditional efforts have been oriented to develop mixtures of yellow pigments from marigold flower with red pigments from chili (*Capsicum annum*). However, it is well known that some products rich in zeaxanthin, like corn gluten, either alone or combined with marigold flower extracts, lead to the same satisfactory results from the commercial point of view. Chemical Abstracts No. 108473z vol. 73, 1970 and No. 145772c vol. 89, 1978, describe the use of xanthophyll based pigments as additives for combined broiler feeds, and more specifically, the use of mixtures of lutein and zeaxanthin with other xanthophylls for coloring egg yolk and broiler skin. Lutein to zeaxanthin ratio determines the specific tonality of the final color imparted by these pigments when used as food additives.

In view of the facts mentioned above, research on different carotenoids has been done in order to produce those having the highest pigmenting activity. It has been found that a high zeaxanthin content in the pigments used as food additives is desirable, and this is one of the reasons why the lutein to zeaxanthin isomerization process has become an important matter for research and development in the poultry pigmenting industry.

Lutein to zeaxanthin isomerization reaction has been known for more than 40 years as it can be verified in some references as Karrer P. et al, published in Helv. Chim. Acta 30, p. 266, 1947, in which such isomerization and others are carried out in the presence of sodium ethoxide.

In the "Acta Chem. Scand." B28 Num. 1, p. 137, 1974 journal, A. G. Andrewes describes a lutein to zeaxanthin isomerization reaction in the presence of polar solvents such as methyl alcohol, potassium methoxide, methyl sulfate and mixtures thereof.

Evidences concerning heat promoted carotenoid isomerization reactions can be found in U.S. Pat. No. 3,989,757, granted on Nov. 2, 1976, in which a carotenoid isomerization process is described. The process comprises heating the carotenoids by means of a water bath at temperatures of from 50 to 120° C.

Development of more accurate analytical techniques, such as the so-called high-performance liquid chromatography (HPLC) has made it possible to determine as a percentage ratio, the lutein and zeaxanthin contents in marigold flower extracts, as well as the percentage ratios obtained after isomerization reactions using state of the art saponification processes.

The papers related to carotenoid hydrolysis mentioned above, describe a wide variety of saponification processes or alkali treatments of marigold flower oleoresins or extracts, carried out under a large diversity of reaction conditions of temperature, pressure, atmosphere, time, quantity and nature of the alkaline substances, solvents, precipitating agents, etc. Also, some evidence can be found of several factors that are able induce carotenoid isomerization, such as high temperature and the presence of an alkali and/or an alcohol.

For these latter reasons, it is not surprising that in some saponification processes of the prior art it has been empirically observed that the zeaxanthin content rises after the saponification, when the temperature also rises beyond certain limits.

Based on the above information and analyzing the prior art, the following hypothesis could be advanced: The improvements in the pigmenting activity described in some of the papers related to the obtention of xanthophylls, were due, in a certain way, to the enhanced absorption of the extract in the broilers, induced by the intake of the free form of the carotenoids produced by the saponification process and, additionally, to an unnoticed partial lutein to zeaxanthin isomerization occurring during the same saponification reaction, which increased the zeaxanthin content, regardless of the fact that the aviculturists did not have any evidence of this circumstance.

Therefore, it can be concluded that traditional saponification processes are carried out together with lutein to zeaxanthin isomerization, inasmuch as it has been empirically observed that the final zeaxanthin content rises when the temperature in the saponification process also rises. It has been also observed that the contents of other carotenoids in the final pigment are modified when higher temperatures are used, thus evidencing that other isomerization reactions are taking place during the traditional saponification reaction, probably due to the high temperature imposed in those processes.

On the other hand, instability of the carotenoids contained in pigments has always been a problem for pigment manufacturers, inasmuch as oxygen, moisture, light and temperature affect these compounds (carotenoid susceptibility to chemical degradation). For this reason, several processes aimed to accomplish the stabilization of xanthophyll compositions can be found in the prior art.

Until now, it has not been possible to achieve a 100% effective method to keep all the xanthophylls contained in plant extracts or in any composition stable when exposed to the environmental noxious factors. Therefore, the above mentioned stabilization processes are only techniques for delaying the degradation of the total carotenoids contained in a composition. For instance, in the aforementioned U.S. Pat. No. 3,523,138, a stabilization method based on temperature control within the scale of from 0 to 150° C. is described. The aforementioned Mexican Certificates of Invention describe stabilization methods based on antioxidant and precipitating agents addition, and U.S. Pat. No. 3,535,426, granted on Oct. 20, 1970, describes a stabilization method of dry marigold flower concentrates using antioxidants, fats and heat exposure.

The above mentioned stabilization processes have had as their main objective the preservation of the initial total carotenoid content in products containing said carotenoids almost unchanged for a long time (at least 6 months approximately), and are used in combination with the traditional saponification or hydrolysis processes.

It has been observed that the lutein to zeaxanthin isomerization yields obtained during the prior art saponification reactions and stabilization processes can be high under high temperature conditions. However, this affects adversely the xanthophyll stability and the zeaxanthin content, inasmuch as it is not high enough for commercial purposes, reason by which, producers in general keep their process conditions only to accomplish the saponification reaction in conventional terms, thus obtaining saponified products having an initial zeaxanthin content of approximately 6% with respect to the total carotenoids, with lutein remaining as the main xanthophyll contained in marigold extracts, inasmuch as lutein seems to be more stable. The isomerization of higher amounts of lutein is accomplished by setting the saponification reaction temperatures to between 50 to 90° C. under various increased pressure conditions.

As the market is demanding nowadays products with high zeaxanthin content, several processes have been developed for producing zeaxanthin only, including from microbiological approaches, such as that referred to in the Chemical Abstract No. 16923v vol. 79, 1973, to chemical syntheses as that published in U.S. Pat. No. 3,558,712. However, until now not one single process capable of obtaining high zeaxanthin concentrations from plant extracts which also preserve the chemical stability of the total carotenoids for a long time, has ever been reported.

U.S. Pat. No. 5,523,494 describes a saponification process by which high zeaxanthin yields can be achieved. However, it has been noted that the product obtained using this process does not possess the necessary chemical stability of the total carotenoids for a long time, inasmuch as said product shows a very short shelf life.

In addition, U.S. Pat. No. 5,780,693, describes a process for the production of zeaxanthin from lutein or an ester thereof, which is based on the documents of Karrer and Andrewes discussed above. U.S. Pat. No. 5,780,693 describes a process carried out at high temperatures and that uses alkali hydroxides in aqueous solutions, instead of potassium methanolate in methanol, as a base, in the presence of dimethyl sulphoxyde (DMSO) as solvent. However, it also mentions that other organic solvents, mainly immiscible in water, can substitute DMSO, provided that an effective amount of a phase transfer catalyst is used. It is important to stress the fact that phase transfer catalysts only improve the mass transfer between the reactants by forming a ion pair that allows the base to migrate from the alkaline aqueous solution to the immiscible organic phase where the other reactant is dissolved, so as to permit the occurrence of the reaction, but without acting as catalysts of the isomerization itself.

In view of the above, for long it has been sought to overcome the drawbacks of the lutein to zeaxanthin isomerization processes of the prior art, by providing an improved process for the isomerization of lutein to zeaxanthin, which in addition to the elimination of the above established disadvantages, could lead to the obtention of a stable product having a zeaxanthin content considerably higher than that obtained by prior art processes.

BRIEF SUMMARY OF THE INVENTION

Having in mind the defects of the prior art, it is an object of the present invention to provide a lutein to zeaxanthin isomerization process, which will allow the obtention of products with high zeaxanthin contents.

Another object of the present invention is to provide a lutein to zeaxanthin isomerization process of the above mentioned character, which will permit to shorten the time in which high yields of lutein to zeaxanthin isomerization are obtained during saponification and stabilization of plant extracts containing lutein.

It is an additional object of the present invention to provide a lutein to zeaxanthin isomerization process of the above nature, which will allow the obtention of a high zeaxanthin content reaction product which can be further treated keeping the stability of the total carotenoid content in a composition for a long time.

DETAILED DESCRIPTION OF THE INVENTION

It has been surprisingly found that, when using surfactants having a Hydrophile-Lipophile Balance (HLB) of from 1 to 40, in a process for the saponification and stabilization of lutein containing plant extracts such as marigold flower, alfalfa, chilli or any extract of a plant variety containing carotenoids, that said surfactant agents act as selective catalytic agents for the lutein to zeaxanthin isomerization.

Among the surfactant agents used as catalytic agents for the lutein to zeaxanthin isomerization, the following can be mentioned in a descriptive, but not limitative manner: propylene glycol, keto-stearyl 20-POE alcohol, ethylene glycol distearate, ammonium lauryl sulfate, sodium lauryl sulfate, triethanol amide lauryl sulfate, alkyl benzene sodium sulfonate, polyglycolic esters of fatty acids, nonyl phenol 30-POE, polyethylene glycol distearate, sorbitan monostearate 20-POE, sorbitan mono-oleate 20-POE, or mixtures thereof.

As mentioned in the background chapter hereinabove, the lutein to zeaxanthin isomerization process of the prior art is accomplished by means of an overheated conventional saponification process, which only permits to obtain low isomerization yields and low chemical stability in respect to the total carotenoid content. It is worth pointing out that the conventional saponification process uses thickening agents such as carboxymethyl cellulose, gelatin or soluble starch, for emulsifying the plant extracts, in order to be able to carry out the saponification using an aqueous alkali solution; however, until now there is no evidence that may indicate that the use of such surfactant agents have as a consequence an increase in the yield of the lutein to zeaxanthin isomerization.

The lutein to zeaxanthin isomerization process of the present invention consists in the addition of the surfactant agent acting as catalyst, during the saponification or alkali treatment of a plant extract containing lutein, maintaining for an additional period of time the reaction temperature. It is important to mention that a saponification of the susceptible compounds of up to 95%, commonly occurs in the first hour of reaction.

The complete process is carried out for a period of time of approximately from 1 to 6 hours, depending on the saponification process, the catalyst and the kind of plant extract used, thus obtaining an approximate lutein conversion yield of from 25 to 96% of the lutein contained initially in the plant extract.

The saponification of the plant extract containing lutein is carried out preferably using concentrated aqueous or alcoholic alkali solutions, such as of sodium hydroxide, potassium hydroxide, calcium hydroxide or mixtures thereof. The alcohols used for preparing the alcoholic solutions are selected from methanol, ethanol, isopropyl alcohol and other low molecular weight alcohols. The saponification reaction is carried out at a temperature range from about 60 to 140° C.; at a reduced or positive pressure, preferably atmospheric pressure; in an inert atmosphere, in an atmosphere with humidity control or at atmospheric conditions, preferably at atmospheric conditions.

The surfactant agents useful as isomerization catalysts, must be present in the saponification reaction in proportions approximately between 1 to 35% by weight of the quantity of the oily plant extract containing lutein, preferably between 5 to 15% by weight approximately.

In accordance with a specific embodiment of the present invention, marigold flower extracts are subjected to the process of the present invention. The saponification of the extracts is carried out in a potassium hydroxide aqueous solution having concentrations at room temperature of approximately from 20 to 70%, preferably 50%, at a reaction temperature approximately between 110 to 120° C. and at atmospheric pressure, without atmosphere control, the preferred catalyst proportions being between 5 to 15% approximately. In this embodiment, the temperature is held between 70 to 140° C. approximately during a period of time of from about 60 to 90 minutes, once the saponification has been completed. The complete process in this embodiment takes from 2 to 3 hours approximately.

Once the process is completed, a reaction product is obtained, which contains zeaxanthin in a range of concentrations of from 20% to 80% of the total carotenoids. The final zeaxanthin content mainly depends on the kind of plant extract to be saponified, on the saponification process used, on the selected catalytic agent and on the stabilization time.

The reaction product obtained can be further purified or directly formulated in different extracts, namely, liquid or solid formulations having high or low zeaxanthin concentrations. Additionally, several inert ingredients can be used according to the final use.

Once having a high zeaxanthin saponified extract, as those obtained by means of the present invention, it is possible to obtain products or compositions having standard carotenoid concentrations and diverse specific zeaxanthin proportions, the obtention of which will not require the relatively difficult and inaccurate control of the conditions of an isomerization process. Instead of depending on the process conditions, by means of the simple mixing of such high zeaxanthin plant extracts with other conventional extracts or pigmenting compositions of commercial type which have low zeaxanthin concentrations, such as Cromophyl-L$^R$ or Cromophyl-20$^R$, it is possible to obtain a wide variety of solid or liquid products having different compositions, in different concentrations or with standardized zeaxanthin proportions.

The following examples are intended to illustrate the present invention in all aspects, but are not to be taken as limitations of the scope thereof.

EXAMPLES

The following examples were carried out by using the prior art saponification process, at a pressure of 1 atmosphere and temperatures around 115° C., with saponification yields near to 100%.

The typical HPLC profile of an oily marigold flower extract used as raw material for the process is shown in Table I.

TABLE I

| HPLC Profile (%) | Raw Material (%) |
| --- | --- |
| β-Carotene | 0.85 ± 0.31 |
| Cryptoxanthin | 1.03 ± 0.88 |
| c-lutein | 1.77 ± 1.40 |
| t-lutein | 74.08 ± 7.44 |
| zeaxanthin | 4.27 ± 1.04 |
| Epoxides | 17.94 ± 6.46 |

Seven tests were carried out in order to demonstrate the effect of several catalytic agents, which results are shown in Table II as well as the HPLC profiles. The tests parameters were as follows:

| PARAMETER | DESCRIPTION | UNIT |
| --- | --- | --- |
| Parameter 1 | Carotenoids in Oleoresin | (carot. g/oil Kg) |
| Parameter 2 | Marigold Flower Oleoresin | (Kg) |
| Parameter 3 | Initial pigment content | (g) |
| Parameter 4 | KOH | (Kg) |
| Paranater 5 | NaOH | (Kg) |
| Parameter 6 | Water | (Kg) |
| Parameter 7 | Catalyst | (Kg) |
| Parameter 8 | Temperature | (° C.) |
| Parameter 9 | Pressure | (Atm) |
| Parameter 10 | Saponification | (%) |
| Parameter 11 | Pigment yield | (%) |

TABLE II

| PARAMETERS | E 0 | E 1 | E 2 | E 3 | E 4 | E 5 | E 6 |
| --- | --- | --- | --- | --- | --- | --- | --- |
| Parameter 1 | 109.0 | 109.0 | 109.0 | 83.0 | 83.0 | 102.0 | 83.0 |
| Parameter 2 | 6.06 | 6.06 | 6.06 | 11.70 | 11.70 | 5.00 | 11.70 |
| Parameter 3 | 660.8 | 660.8 | 660.8 | 971.1 | 971.1 | 510.0 | 971.1 |
| Parameter 4 | 1.05 | 1.05 | 1.05 | 2.03 | 2.03 | 0.94 | 2.03 |
| Parameter 5 | 0.14 | 0.14 | 0.14 | 0.28 | 0.28 | 0.13 | 0.28 |
| Parameter 6 | 1.288 | 1.288 | 1.288 | 2.500 | 2.500 | 1.160 | 2.500 |
| Parameter 7 | 0.00 | 0.48 | 0.48 | 0.94 | 0.94 | 0.44 | 0.94 |
| Parameter 8 | 120.0 | 113.0 | 115.0 | 117.0 | 113.0 | 117.0 | 112.0 |
| Parameter 9 | 1.0 | 1.0 | 1.0 | 1.0 | 1.0 | 1.0 | 1.0 |
| Parameter 10 | 99.70 | 99.32 | 98.81 | 99.13 | 100.52 | 101.67 | 100.10 |
| Parameter 11 | 95.5 | 90.5 | 95.0 | 89.6 | 83.2 | 82.2 | 81.6 |
| HPLC (%) | | | | | | | |
| β-Carotene | 0.62 | 1.28 | 2.26 | 0.90 | 0.70 | 0.69 | 9.69 |
| Cryptoxanthin | 3.98 | 4.93 | 5.92 | 6.73 | 6.37 | 4.35 | 4.64 |
| c-Lutein | ND | 0.27 | 0.19 | 0.18 | 0.34 | 0.18 | 0.15 |
| t-Lutein | 77.20 | 54.16 | 17.88 | 19.14 | 33.73 | 35.27 | 24.19 |
| Zeaxanthin | 7.59 | 22.38 | 65.54 | 65.73 | 42.66 | 48.75 | 61.07 |
| Epoxides | 10.61 | 16.98 | 8.22 | 7.33 | 19.19 | 40.75 | 9.28 |

ND=Non Detected

The seven tests referred to in Table II, were carried out under similar reaction time conditions. The reference test (E0), was carried out under the same process conditions as the others but without any catalyst addition.

Tests 1 to 6 (E1 to E6) were carried out in the presence of different catalytic agents. In all of these cases, it was observed that the reaction products obtained showed a zeaxanthin content higher than that obtained for the reference test (E0).

The catalytic agents used in tests 1 to 6 were added in quantities of around 8% by weight in respect to the marigold flower oleoresin, according to the following: propylene glycol for Test 1 (E1), sorbitan mono-oleate 20-POE for Test 2 (E2), nonil phenol 30-POE in Test 3 (E3), alkyl benzene sodium sulfonate in Test 4 (E4), triethanol amide lauryl sulfate in Test 5 (E5) and lauryl alcohol 10-POE in Test 6 (E6).

As it can be seen from the results of the tests shown above, the action of the catalytic agents in respect to the increase of zeaxanthin content in the final pigment is evident, inasmuch as, although Test 1 (E1) shows a lower final zeaxanthin content than the other catalyzed tests, this content is still around tree times higher than the zeaxanthin content in the (E0) reference test.

It is worth to point out that in the tests in which a surfactant was used as catalyst (E1 to E6), a stable pigment (final product) was obtained in respect to the total carotenoid content, which showed good stability in long term shelf-life tests.

In order to demonstrate the stability of the pigments obtained from the reaction product of the present invention, Test 7 and 8 were carried out (E7 and E8), which results are shown in Table III, according to the following:

| TEST | Propylene glycol (%)* | Sorbitan Mono Oleate 20-POE (%)* |
| --- | --- | --- |
| E7 | 0 | 0 |
| E8 | 18 | 10 |

(* = Weight percent of the amount of crude marigold flower extract).

The process conditions such as stirring, reaction time, pressure and temperature were the same for both tests. The reaction products obtained were formulated and analyzed before and after being subjected to challenge or fast degradation conditions consisting in heating the corresponding samples at 75° C. for 72 hours. The results are shown in Table III.

TABLE III

| FAST DEGRADATION | BEFORE TEST | | AFTER TEST | |
| --- | --- | --- | --- | --- |
| | E7 | E8 | E7 | E8 |
| Pigment Conc. (g/kg) | 14.07 | 12.68 | 6.72 | 11.16 |
| Degradation (%) | | | 52.2 | 12.0 |

The results shown above demonstrate that for Test 7 (E7), the pigment degradation was 52.2%, more than two times the degradation observed on the product obtained by means of the process of the present invention, in which, according to Test 8 (E8), a degradation of only 12% of the original pigment content was obtained.

Although certain specific embodiments of the present invention have been shown and described above, it must be emphasized that numerous modifications thereof are possible. The present invention, therefore, will not be considered as limited, except by the requirements of the prior art and the spirit of the enclosed claims.

What is claimed is:

1. A lutein to zeaxanthin isomerization process comprising the saponification or alkali treatment of a plant extract containing lutein, followed by a heating period, wherein the saponification or alkali treatment and heating period are carried out in the presence of a catalyst for the lutein to zeaxanthin isomerization reaction and at a temperature of from about 60 to 140° C., thus obtaining an approximate yield of 25 to 96% of conversion of the lutein contained in the plant extract, the catalyst being a surfactant which is suitable for use in food or feed additives and which has a Hydrophile-Lipophile Balance of between 1 and 40, wherein the catalyst is selected from the group consisting of propylene glycol, keto-stearyl 20-POE alcohol, ethylene glycol distearate, ammonium lauryl sulfate, sodium lauryl sulfate, triethanol amide lauryl sulfate, alkyl benzene sodium sulfonate, polyglycolic esters of fatty acids, nonyl phenol 30-POE, polyethylene glycol distearate, sorbitan monostearate 20-POE, sorbitan mono oleate 20-POE, or mixtures thereof.

2. A lutein to zeaxanthin isomerization process according to claim 1, wherein the surfactant is present in a proportion of from about 1 to 35% by weight of the plant extract containing lutein.

3. A lutein to zeaxanthin isomerization process according to claim 2, wherein the plant extract containing lutein is selected from an extract of marigold flower, alfalfa, chilli and any other plant variety containing carotenoids.

4. A lutein to zeaxanthin isomerization process according to claim 3, wherein the plant extract containing lutein is marigold flower extract and the amount of surfactant employed is from about 5 to 15% by weight of the plant extract containing lutein.

5. A lutein to zeaxanthin isomerization process according to claim 2, wherein the saponification or alkali treatment is carried out by treating the plant extract containing lutein with an aqueous solution of an alkali selected from sodium hydroxide, potassium hydroxide, calcium hydroxide or mixtures thereof, at a temperature approximately between 60 and 140° C.; and the heating period is carried out at a temperature of approximately between 60 and 140° C.

6. A lutein to zeaxanthin isomerization process according to claim 2, wherein the saponification or alkali treatment is carried out by treating the plant extract containing lutein with an alcoholic solution of an alkali selected from sodium hydroxide, potassium hydroxide, calcium hydroxide or mixtures thereof.

7. A lutein to zeaxanthin isomerization process according to claim 6, wherein the alcoholic solution is prepared with a low molecular weight alcohol selected from methanol, ethanol, isopropyl alcohol and mixtures thereof.

8. A lutein to zeaxanthin isomerization process according to claim 5, wherein the plant extract containing lutein is marigold flower extract; the saponification reaction is carried out by using an aqueous solution of potassium hydroxide with a concentration of from about 20 to 70% by weight, at a temperature of 110 to 120° C. and at atmospheric pressure; and the heating period is carried out at a temperature of between 70 to 140° C., during 60 to 90 minutes, approximately, thus obtaining a reaction product containing up to approximately 80% of zeaxanthin of the total carotenoids.

9. A lutein to zeaxanthin isomerization process according to claim 8 wherein the saponification reaction is carried out by using an aqueous solution of potassium hydroxide with a concentration of about 50% by weight.

10. A lutein to zeaxanthin isomerization process according to claim 8 wherein an additional mixing step is performed by mixing the reaction product with a pigmenting composition having low zeaxanthin concentration, in order to obtain a pigmenting composition which is stable in respect to the total carotenoid concentration for long periods of time.

* * * * *